US009480494B2

(12) United States Patent
McGhie (10) Patent No.: US 9,480,494 B2
(45) Date of Patent: Nov. 1, 2016

(54) HELICALLY ADVANCING CONSTRICTION CROSSING MECHANISM AND WIRE GUIDE POSITIONING METHOD FOR PERFORMING PERCUTANEOUS VASCULAR PROCEDURES (71) Applicant: Cook Medical Technologies LLC, Bloomington, IN (US)

(72) Inventor: Thomas McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 201 days.

(21) Appl. No.: 14/089,128

(22) Filed: Nov. 25, 2013

(65) Prior Publication Data
US 2014/0088626 A1  Mar. 27, 2014

Related U.S. Application Data (62) Division of application No. 12/648,429, filed on Dec. 29, 2009, now Pat. No. 8,597,314.

(51) Int. Cl.
*A61B 17/22* (2006.01)
*A61B 17/3207* (2006.01)

(52) U.S. Cl.
CPC ... *A61B 17/320725* (2013.01); *A61B 17/3207* (2013.01); *A61B 2017/22044* (2013.01); *A61B 2017/22048* (2013.01); *A61B 2017/22069* (2013.01); *A61B 2017/22094* (2013.01)

(58) Field of Classification Search
CPC .................. A61B 17/3207; A61B 17/320725; A61B 2017/22044; A61B 2017/22048; A61B 2017/22069; A61B 2017/22094
See application file for complete search history.

(56) References Cited

U.S. PATENT DOCUMENTS

| 4,732,154 | A | * | 3/1988 | Shiber .............. A61B 17/22012 606/108 |
| 4,926,858 | A | * | 5/1990 | Gifford, III ...... A61B 17/22031 604/22 |
| 5,217,482 | A | | 6/1993 | Keith |
| 5,334,211 | A | | 8/1994 | Shiber |
| 5,429,597 | A | | 7/1995 | DeMello et al. |
| 5,601,537 | A | | 2/1997 | Frassica |
| 5,766,184 | A | | 6/1998 | Matsuno et al. |
| 5,776,142 | A | | 7/1998 | Gunderson |

(Continued)

FOREIGN PATENT DOCUMENTS

| EP | 0657140 | 6/1995 |
| WO | 2007103161 | 9/2007 |
| WO | 2011081956 | 7/2011 |

*Primary Examiner* — Julie A Szpira
(74) *Attorney, Agent, or Firm* — Liell & McNeil (57) ABSTRACT A vascular procedure includes sliding a constriction crossing mechanism over a wire guide having a tip positioned at a proximal side of a constriction, and rotating a sheath of the mechanism about an axis relative another sheath of the mechanism. The method further includes helically engaging the sheaths, and guiding an intraluminal treatment device into or past the constriction. The mechanism includes a first sheath and a second sheath, and a tip coupled with the first sheath. The mechanism further includes a helical coupling between the first and second sheaths, which is configured to convert a torque on one of the sheaths to an axial force on the other of the sheaths for crossing a vascular constriction with the tip. An anchoring mechanism coupled with one of the sheaths includes a deployed state resisting displacement of the second sheath within a vascular structure of a patient.

10 Claims, 4 Drawing Sheets

(56) References Cited

U.S. PATENT DOCUMENTS

| | | |
|---|---|---|
| 5,807,330 A | 9/1998 | Teitelbaum |
| 5,882,334 A | 3/1999 | Sepetka et al. |
| 6,113,579 A | 9/2000 | Eidenschink et al. |
| 6,206,898 B1 | 3/2001 | Honeycutt et al. |
| 6,245,030 B1 | 6/2001 | DuBois et al. |
| 6,258,064 B1 | 7/2001 | Smith et al. |
| 6,379,334 B1 | 4/2002 | Frassica |
| 6,595,959 B1 | 7/2003 | Stratienko |
| 2004/0102719 A1 | 5/2004 | Keith et al. |
| 2005/0049574 A1 | 3/2005 | Petrick et al. |
| 2005/0143768 A1 | 6/2005 | Shiber |
| 2005/0228475 A1 | 10/2005 | Keeble et al. |
| 2006/0079812 A1* | 4/2006 | Viswanathan ........ A61M 25/09 600/585 |
| 2006/0293612 A1* | 12/2006 | Jenson ............... A61B 17/3207 600/585 |
| 2009/0306597 A1* | 12/2009 | Lupton ............ A61B 17/3207 604/164.13 |

\* cited by examiner

HELICALLY ADVANCING CONSTRICTION CROSSING MECHANISM AND WIRE GUIDE POSITIONING METHOD FOR PERFORMING PERCUTANEOUS VASCULAR PROCEDURES

CROSS-REFERENCE TO RELATED APPLICATION

This patent application is a divisional of U.S. patent application Ser. No. 12/648,429, filed Dec. 29, 2009, now U.S. Pat. No. 8,597,314.

TECHNICAL FIELD

The present disclosure relates generally to the field of peripheral intervention in the cardiovascular system, and relates more particularly to crossing a vascular constriction with a helically advancing constriction crossing mechanism.

BACKGROUND

Partial or total occlusions can form throughout the cardiovascular system of human patients. Such occlusions limit normal blood flow, and can cause a variety of health problems. Medical professionals have developed a wide variety of techniques for treating occlusions such as angioplasty, tissue removal and stents. To perform such techniques, percutaneous entry is employed in a well known manner to gain access to occlusions or other vascular constrictions within a patient. Percutaneous entry generally involves the creation of an incision in a patient's skin to enable positioning an intraluminal treatment device within the vasculature of a patient. Wire guides are typically employed to guide an intraluminal treatment device to a location of interest where a procedure such as angioplasty is performed. It may be necessary to pass a wire guide along a relatively tortuous path, often a meter or longer, to reach the location where angioplasty or another technique is to be performed.

Properly positioning a wire guide to enable guiding the intraluminal treatment device may include negotiating turns and branches within the patient's vasculature. The occlusion to be treated may itself include a constriction in the patient's vasculature which is difficult to pass with the wire guide. Similarly, other constrictions may lie in the desired travel path of the wire guide to a target location. Crossing such constrictions may create challenges for clinicians. While some axial force may be applied to a wire guide to push past a vascular constriction, substantially loading a wire guide in axial compression in an attempt to push through a vascular constriction risks injury to the patient, such as vascular wall puncturing.

Medical professionals have proposed a variety of techniques for crossing vascular constrictions. Among these are specialized ways to orient a wire guide tip, or stiffen a wire guide or other device, to enable successful crossing of the constriction without creating an undue risk to the patient. While certain of these techniques have proven successful, there remains room for improvement.

SUMMARY OF THE DISCLOSURE

In one aspect, a vascular constriction crossing mechanism includes a first sheath having a proximal segment and a distal segment, and defining a longitudinal axis, and a second sheath also having a proximal segment and a distal segment, and defining a longitudinal axis. The vascular constriction crossing mechanism further includes a constriction crossing tip coupled with the distal segment of the first sheath, and a helical coupling between the first sheath and the second sheath. The helical coupling is configured to convert a torque on the proximal segment of one of the first sheath and the second sheath to an axial force on the first sheath for crossing a vascular constriction with the constriction crossing tip. The vascular constriction crossing mechanism further includes an anchoring mechanism having a rest state, and a deployed state, the deployed state including a vascular wall contact state whereby the anchoring mechanism resists displacement of the second sheath within a vascular structure of a patient.

In another aspect, a method of positioning a wire guide includes sliding a vascular constriction crossing mechanism in a proximal to distal direction over a wire guide having a wire guide tip positioned at a first location, and rotating one of a first sheath of the vascular constriction crossing mechanism and a second sheath of the vascular constriction crossing mechanism about an axis of rotation relative to the other of the first sheath and the second sheath. The method further includes advancing a constriction crossing tip of the first sheath in the proximal to distal direction at least in part by helically engaging the first sheath with the second sheath during the step of rotating. The method further includes positioning the wire guide tip at a second location which is distal to the first location at least in part by advancing the wire guide in the proximal to distal direction subsequent to advancing the constriction crossing tip.

In still another aspect, a method of performing a percutaneous vascular procedure on a patient includes sliding a vascular constriction crossing mechanism in a proximal to distal direction over a wire guide having a wire guide tip positioned at a first location on a proximal side of a vascular constriction. The method further includes rotating one of a first sheath of the vascular constriction crossing mechanism and a second sheath of the vascular constriction crossing mechanism about an axis of rotation relative to the other of the first sheath and the second sheath. The method further includes advancing a constriction crossing tip of the first sheath through the vascular constriction to a second location which is distal to the first location at least in part by helically engaging the first sheath with the second sheath during the step of rotating, and guiding an intraluminal treatment device to the second location.

DETAILED DESCRIPTION

Figure 1:
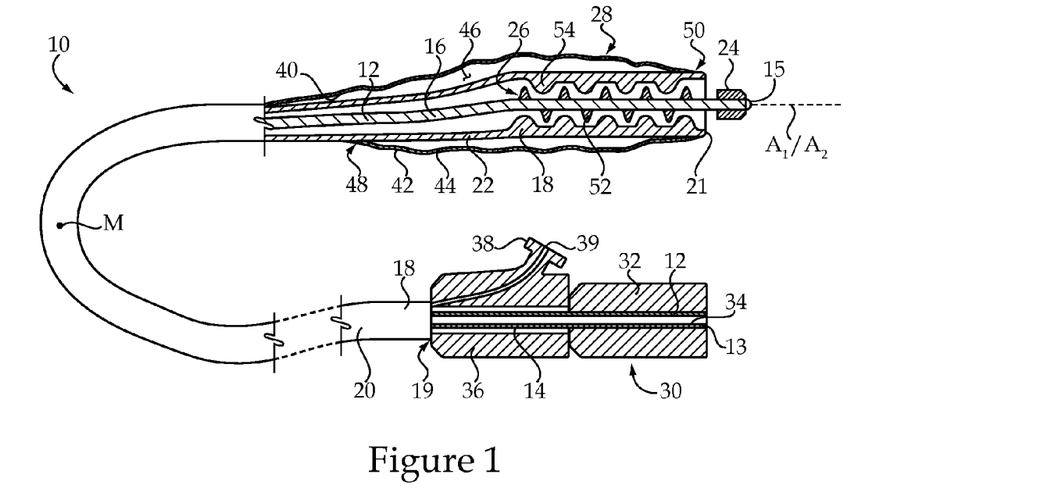
FIG. 1 is a partially sectioned side diagrammatic view of a vascular restriction crossing mechanism, according to one embodiment.

Referring to FIG. 1, there is shown a vascular constriction crossing mechanism 10 according to one embodiment. As will be further apparent from the following description, mechanism 10 is of a type suitable for use in performing a percutaneous vascular procedure on a patient such as a human patient. Mechanism 10 may include a first sheath 12 having a proximal segment 14 and a distal segment 16, and defining a longitudinal axis $A_1$. First sheath 12 may further include a proximal end 13 which includes a terminal end, and a distal end 15 which also includes a terminal end. A constriction crossing tip 24 may be coupled with distal segment 16 and configured for crossing a vascular constriction, as further described herein. It will generally be desirable for tip 24 to include an atraumatic tip, having characteristics such as shape, materials and/or surface texture such that tip 24 will slide relatively easily past or through vascular tissue and/or deposits such as plaque accumulated within a vascular structure such as a vein or artery. First sheath 12 may further define a wire guide lumen 34 extending between proximal end 13 and distal end 15. During use, a wire guide (not shown in FIG. 1) may extend through wire guide lumen 34, enabling guiding of mechanism 10 to and from a location of interest within the vasculature of a patient. Wire guide lumen 34 is shown opening at and accessible from proximal end 13 of sheath 12. In other embodiments, a system might be used such that wire guide lumen 34 is accessed distally of proximal end 13 to reduce a length of the wire guide used, or for other known purposes. Mechanism 10 may further include a second sheath 18 also having a proximal end 19 and a distal end 21, a proximal segment 20 and a distal segment 22, and also defining a longitudinal axis $A_2$. In the embodiment shown, second sheath 18 includes an outer sheath positioned about first sheath 12, which may include an inner sheath, and arranged co-axially therewith.

Mechanism 10 may further include a handle mechanism 30 having a first handle 34 coupled with first sheath 12 and a second handle 36 coupled with second sheath 18. In one embodiment, handles 34 and 36 may be configured such that one may be rotated relative to the other to induce relative rotation between sheaths 12 and 18 respectively coupled therewith, for reasons further explained herein. Mechanism 10 may further include a helical coupling 26 between first sheath 12 and second sheath 18. Helical coupling 26 is configured to convert a torque on one of proximal segments 14 and 20 to an axial force on first sheath 12 for crossing a vascular constriction with constriction crossing tip 24, as further described herein. In one embodiment, helical coupling 26 may include a screw element 52 located on one of distal segments 16 and 22. Relative rotation between first sheath 12 and second sheath 18 may induce helical engagement between first sheath 12 and second sheath 18 to cause one of sheaths 12 and 18 to be axially displaced relative to the other of sheaths 12 and 18. Accordingly, relative rotation between handles 34 and 36 in a first direction of relative rotation can cause screw element 52 to helically engage with sheath 18 to cause first sheath 12 to advance relative to second sheath 18 in a proximal to distal direction. Relative rotation between handle 34 and handle 36 in a second direction of relative rotation can cause first sheath 12 to retract in a distal to proximal direction relative to second sheath 18.

In the embodiment depicted in FIG. 1, screw element 52 may include an external thread located on distal segment 16 of first sheath 12. Helical coupling 26 may further include an internal thread 54 located on distal segment 22 of second sheath 18. It is contemplated that cooperating threads 52 and 54 may provide one practical implementation strategy. The present disclosure is not thereby limited, however, and alternative strategies are contemplated such as a self-tapping external thread located on first sheath 12 which is configured to helically advance through relatively soft material of second sheath 18. A self-tapping internal thread on second sheath 18 might also be used. In still further embodiments, rather than a continuous internal thread cooperating with a continuous external thread, multiple threads or multiple partial threads might be used for either of thread 52 or thread 54. Thus, the term "thread" and the present description should not be construed herein in a limiting sense to require a specific thread configuration, thread number or other thread characteristics. A variety of mechanisms capable of inducing the described axial advancement in response to a torque on one of sheath 12 and sheath 18 would fairly be said to include a helical coupling, or for that matter a thread. It should further be appreciated that thread pitch might be tailored to provide or enhance certain functional characteristics of device 10 during rotating handles 34 or 36 relative to one another. For example, thread 52 and thread 54 might be designed having a relatively steeper pitch to result in a relatively large displacement per turn of handle 34 relative to handle 36. Alternatively, relatively less steep threads might be used to provide a lesser displacement per turn of handle 34 relative to handle 36. Such a design may reduce the relative effort on the part of a clinician to advance tip 24 through a vascular constriction, as further described herein, and may also provide for relatively fine control over axial positioning of tip 24.

In one embodiment, external thread 52 may be fashioned by adhering a coil of material such as a metallic wire to an outer diameter of sheath 12, for instance via an adhesive. Thread 54 may be made by adhering another coil of material to the inner diameter of sheath 18. In other embodiments, thread 52 and thread 54 might be manufactured by way of known machining techniques. In still further embodiments, a threaded mandrel might be used as a mold or die against which molten or softened material of sheath 12 or sheath 18 is allowed to harden. The threaded mandrel can then be removed to result in the desired threaded configuration. All the components of device 10 may be made from known materials and by way of known manufacturing techniques. Sheaths 12 and 18, for example may be made from catheter materials of the type used in the manufacturing of certain flexible catheters by Cook Incorporated, the Assignee of the present patent application. Threads 52 and 54 may be made of the same catheter material or known materials compatible for use therewith. Threads 52 and 54 might also include relatively harder materials such as metallic materials. In one practical implementation strategy, sheath 12, and possibly also sheath 18, may include materials such as polyetherether ketone and have a braided construction to enhance torque response during rotating the subject sheath with handle mechanism 30. It should nevertheless be appreciated that sheaths 12 and 18 as well as the other components of mechanism 10 are not limited to any specific materials or manufacturing techniques. The use of radiopaque materials may be desirable for at least portions of mechanism 10, for reasons well known in the art.

Vascular constriction crossing mechanism 10 may further include an anchoring mechanism 28 having a rest state and a deployed state. The deployed state may include a vascular wall contact state whereby anchoring mechanism 28 resists displacement of second sheath 18 within a vascular structure of a patient. As will be further explained herein, converting a torque on one of handles 32 and 36 to an axial displacement force on sheath 12 will tend to generate an opposing axial displacement force on sheath 18. In other words, rotation of one of handles 32 and 36 will tend to urge sheath 12 in an axially advancing proximal to distal direction. A counter-force will tend to be generated, however, which will tend to urge sheath 18 in an opposite direction. A vascular constriction may resist penetration or passing of tip 24 therethrough. Anchoring mechanism 28 may be deployed to frictionally engage against a vascular wall of a patient to resist displacing second sheath 18 when constriction crossing tip 24 is advanced through a vascular constriction. It may also be appreciated that relative rotation between handles 32 and 36, and the resultant relative rotation between sheath 12 and sheath 18, may tend to induce a rotational displacement force on second sheath 18. In other words, as first sheath 12 is rotated, a torque may be applied to second sheath 18 by way of the engagement of thread 52 with thread 54. Deploying anchoring mechanism 28 against a vascular wall of the patient may likewise resist rotational displacement forces on second sheath 18.

A variety of configurations and deployment strategies for anchoring mechanism 28 are contemplated. In one embodiment, anchoring mechanism 28 might include a system of one or more control wires which extend in parallel with sheath 18 and contact a radially expandable mechanism mounted on or in sheath 18. By manipulating such control wires, the radially expandable mechanism might be pushed outwardly from a rest state to a deployed state at which the mechanism contacts a vascular wall of the patient to frictionally engage therewith. It is contemplated that a practical implementation strategy, however, may employ a fluid expandable anchoring mechanism. To this end, second sheath 18 may define an anchoring control lumen 40 which extends between proximal end 19 and distal end 21. Anchoring control lumen 40 may include a fluid passage for delivery of an inflation fluid such as a mixture of saline and contrast agent to anchoring control mechanism 28 from a location outside of a patient. Handle 36 may include a fitting 38 having a fluid port 39 formed therein which extends through handle 36 and is in fluid communication with anchoring control lumen 40. Anchoring mechanism 28 may further include an expandable anchor 42 having a flexible wall 44 attached to sheath 18 and configured to expand from a rest state to a deployed state via the introduction of fluid through anchoring control lumen 40 to a fluid cavity 46 defined in part by flexible wall 44 and in part by sheath 18. Flexible wall 44 may be formed from relatively soft silicone or silicone containing materials which allow for inflation via relatively low pressure inflation fluid. In one embodiment, inflation fluid may be provided for deploying mechanism 28 at a pressure of less than four atmospheres, and possibly a pressure less than three atmospheres. Radiography may be used to assist a clinician in determining mechanism 28 has been properly deployed. It will typically be desirable to contact anchoring mechanism 28 with a vascular wall of a patient without plastically deforming the vascular wall. To this end, it may be appreciated that anchoring mechanism 28 will typically have a construction and function different from higher pressure peripheral intervention devices such as angioplasty balloons, which may induce plastic deformation of vascular tissue and plaques, lesions, etc.

In the embodiments shown, anchoring mechanism 28 is illustrated positioned on distal segment 22 of second sheath 18. Sheath 18 may further include a length extending from proximal end 19 to distal end 21 and having a midpoint M. Flexible wall 44 may extend circumferentially around second sheath 18 and includes a first end 48 sealingly attached to second sheath 18 at a first location which is distal to midpoint M, and a second end 50 sealingly attached to second sheath 18 at a second location which is also distal to midpoint M. In other embodiments, anchoring mechanism 28 might be positioned proximally of the location shown in FIG. 1. In other words, it is not necessary that anchoring mechanism 28 be positioned as close to distal end 21 of second sheath 18 as that depicted. It may nevertheless be desirable in a practical implementation strategy to locate anchoring mechanism 28 somewhere on distal segment 22, as opposed to proximal segment 20. It has been observed that imparting axial forces to mechanism 10 in vivo, either by way of pushing handle mechanism 30 in a proximal to distal direction, or by way of inducing relative rotation between first sheath 12 and second sheath 18, may load sheath 12 in axial compression. By positioning anchoring mechanism 28 on distal segment 22, axial compression of first sheath 12 during advancing through a vascular constriction can be limited to portions of first sheath 12 distal to anchoring mechanism 28. In other words, anchoring mechanism 28 can provide a "foothold," reacting axial displacement forces on mechanism 10, and thus preventing axial loading of portions of mechanism 10 proximal to anchoring mechanism 28, as further described herein.

Figure 2:
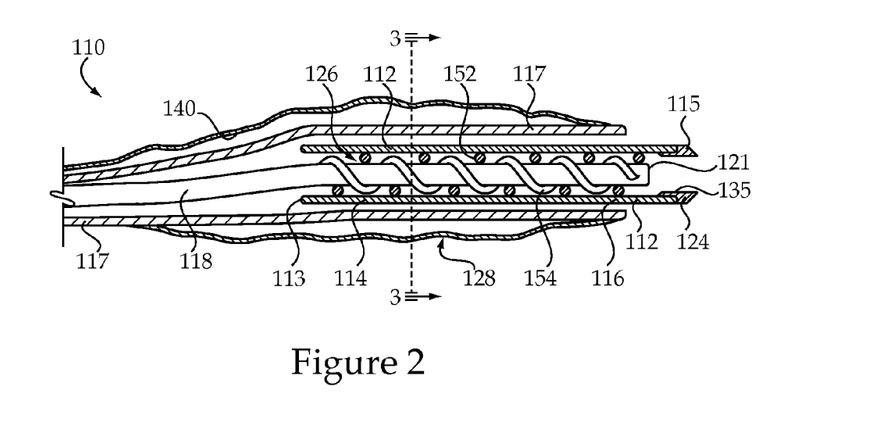
FIG. 2 is a partially sectioned side diagrammatic view of a portion of a vascular constriction crossing mechanism, according to another embodiment.

Turning now to FIG. 2, there is shown a vascular constriction crossing mechanism 110 according to another embodiment. Mechanism 110 includes certain similarities with mechanism 10 described above, but also has certain differences. Like mechanism 10, vascular constriction crossing mechanism 110 may include a system of coaxial sheaths including a first sheath 112 and a second sheath 118, and a helical coupling 126 configured to advance first sheath 112 relative to second sheath 118 across or through a vascular constriction within a patient. First sheath 112 includes a proximal end 113 which is a terminal end, a distal end 115 which is also a terminal end, a proximal segment 114 and a distal segment 116, and a constriction crossing tip 124 coupled with distal segment 116. Second sheath 118 also includes a proximal segment (not shown) and a distal segment which is shown in FIG. 2. It may be noted that first sheath 112 includes an outer sheath, whereas second sheath 118 includes an inner sheath. Helical coupling 126 may include a screw element 152 located on first sheath 112 which includes an internal thread 152. Helical coupling 126 may further include an external thread 154 located on second sheath 118. Mechanism 110 may further include an anchoring mechanism 128 having a configuration and operation similar to that of vascular constriction crossing mechanism 10. In contrast to vascular constriction crossing mechanism 10, mechanism 110 may include a second outer sheath 117 positioned about first sheath 112 and second sheath 118. Anchoring mechanism 128 may be attached to second outer sheath 117, and may further define an anchoring control lumen 140 for supplying an inflation fluid to anchoring mechanism 128. In operation, relative rotation between first sheath 112 and second sheath 118, which may be induced by rotating second sheath 118, will tend to cause first sheath 112 to be axially displaced by way of helical engagement between internal thread 152 and external thread 154.

Figure 3:
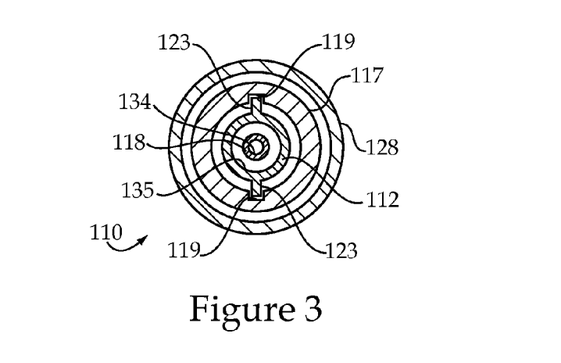
FIG. 3 is a sectioned view taken along line 3-3 of FIG. 2.

Referring also to FIG. 3, there is shown a sectioned view taken along line 3-3 of FIG. 2. During rotation of second sheath 118 relative to first sheath 112 it may be desirable to restrict rotation of first sheath 112. To this end, second outer sheath 117 slidably journals first sheath 112. In one particular embodiment, second outer sheath 117 may define one or more longitudinal channels 119 receiving corresponding tabs 123 located on first sheath 112. Tabs 123 and channels 119 are not illustrated in FIG. 2 for purposes of clarity. When a torque is applied to rotate second sheath 118, rather than inducing rotation of first sheath 112, an interaction between tabs 123 and channels 119 results in the relative rotation driving first sheath 112 in a proximal to distal direction for crossing a vascular constriction, or a distal to proximal direction for retracting out of a vascular constriction, depending upon the direction of rotation of second sheath 118 relative to first sheath 112. Those skilled in the art will appreciate that when anchoring mechanism 128 is deployed, second sheath 118 may be rotated to induce axial advancement or retraction of first sheath 112 without displacing second sheath 118. Thus, a distal end 121 of second sheath 118 may remain stationary. Although not illustrated, a handle mechanism similar to handle mechanism 30 shown in FIG. 1 might be used with vascular constriction crossing mechanism 110. As shown in FIG. 3, second sheath 118 may define a wire guide lumen 134 through which a wire guide is passed from a location outside of a patient during performing a percutaneous vascular procedure. First sheath 112 may define a second wire guide lumen 135 in communication with wire guide lumen 134, through which the wire guide is passed beyond distal end 121 of second sheath 118.

INDUSTRIAL APPLICABILITY

Figure 4:
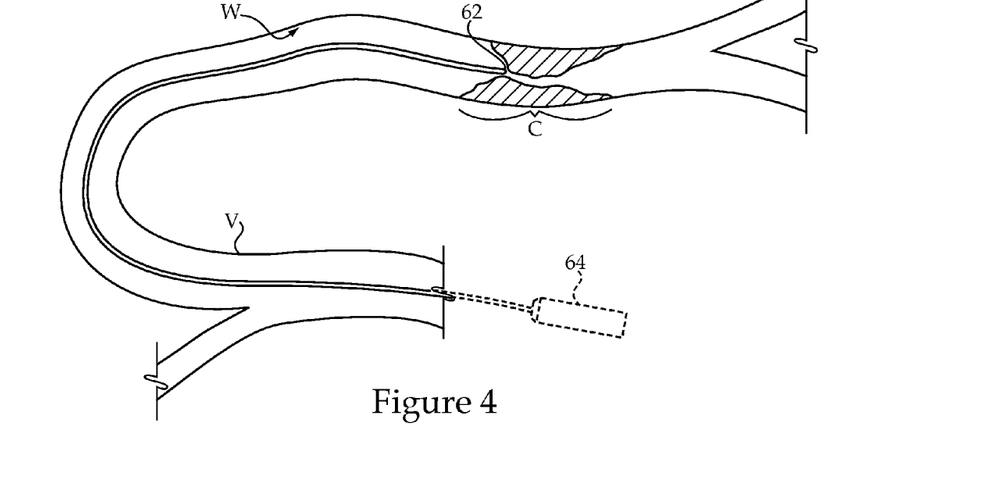
FIG. 4 is a side diagrammatic view of a vascular structure of a patient, at one stage of a procedure, according to one embodiment.

Referring to FIG. 4, there is shown a vascular structure V of a patient having a wire guide 60 positioned therein, at a first stage of a procedure according to one embodiment. The procedure, further described herein, may include a percutaneous vascular procedure such as an angioplasty procedure, a stent placement or retrieval procedure, a vascular filter placement or retrieval procedure, an imaging procedure, or any other known procedure where it is necessary or desirable to position an intraluminal treatment device within or beyond a vascular constriction in a patient. Vascular constrictions amenable to crossing via the techniques and devices described herein include calcified adenomas, for example. The present disclosure is not limited in this regard, however, and other vascular constrictions resulting from the build-up of material within a vascular structure of a patient, trauma, scarring, or even congenital abnormalities, might be advantageously crossed or accessed according to the teachings set forth herein. Wire guide 60 may include a distal end having a distal tip 62, and a proximal end coupled with a manipulation handle 64. Wire guide 60 is shown in FIG. 4 as it might appear after having been passed through vascular structure V along a curving path to a point proximal to or slightly within a vascular constriction C. As further described herein, performing a percutaneous vascular procedure on a patient may include assisting crossing vascular constriction C with wire guide 60, to position wire guide tip 62 at a second location which is distal to its location depicted in FIG. 4.

Figure 5:
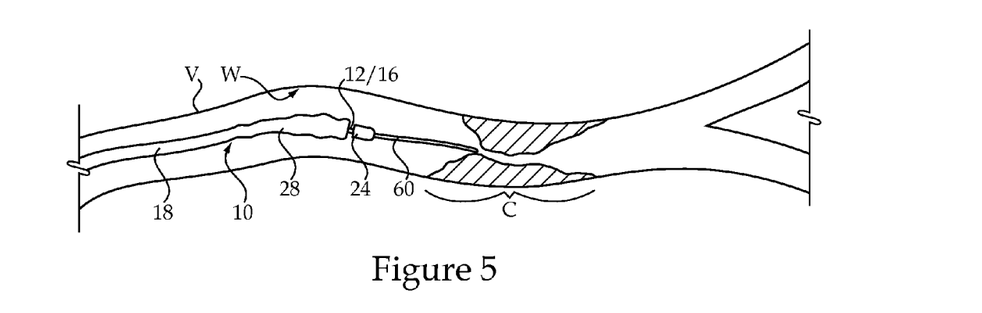
FIG. 5 is a side diagrammatic view of a vascular structure of a patient, at another stage of a procedure, according to one embodiment.

A clinician will typically manipulate wire guide 60 to the position depicted in FIG. 4 with the assistance of radiography. Wire guide 60 may be relatively flexible at wire guide tip 62, and thus visual determination by the clinician that wire guide tip 62 has reached vascular constriction C may take place. In other instances, the clinician might be able to determine that wire guide tip 62 has reached vascular constriction C at least in part by sensing a resistance to further advancement of wire guide 60 while manipulating handle 64. When it is determined that assistance in crossing vascular constriction C with wire guide 60 is desired, the clinician may slide a vascular constriction crossing mechanism such as mechanism 10 or mechanism 110 described herein in a proximal to distal direction over wire guide 60. Referring now to FIG. 5, there is shown vascular structure V having vascular constriction crossing mechanism 10 positioned over wire guide 60 and having been slid in the proximal to distal direction to reach the vicinity of vascular constriction C. It may be noted that anchoring mechanism 28 is in a rest state and also that constriction crossing tip 24 is yet to be axially advanced relative to second sheath 18. Distal segment 16 of first sheath 12 is visible extending between constriction crossing tip 24 and second sheath 18. Prior to positioning mechanism 10 within a patient, a fluid such as water or saline may be flushed through device 10 to expel air bubbles.

Figure 6:
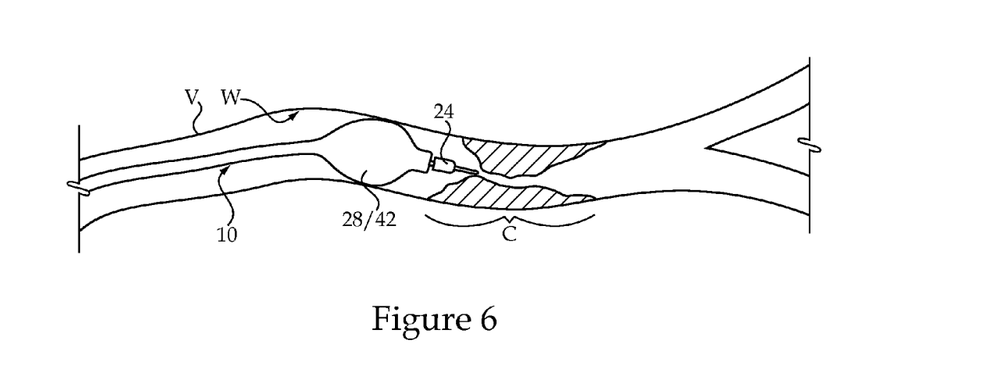
FIG. 6 is a side diagrammatic view of a vascular structure of a patient, at yet another stage of a procedure, according to one embodiment.

Referring now to FIG. 6, there is shown vascular structure V wherein anchoring mechanism 28 of constriction crossing mechanism 10 has been deployed to contact expandable anchor 42 with a vascular wall W of vascular structure V. It will be recalled that deploying anchoring mechanism 28 will provide a "foothold" for resisting rotational and axial displacement of second sheath 18 when first sheath 12 and constriction crossing tip 24 are axially advanced to cross a vascular constriction. It will further be recalled that expandable anchor 42 may be expanded from a rest state, approximately as shown in FIG. 5, to a deployed state, approximately as shown in FIG. 6, by supplying an inflation fluid through anchoring control lumen 40. It will still further be recalled that anchoring mechanism 28 may be deployed to contact a vascular wall of the patient without plastically deforming the vascular wall.

Figures 7, 8:
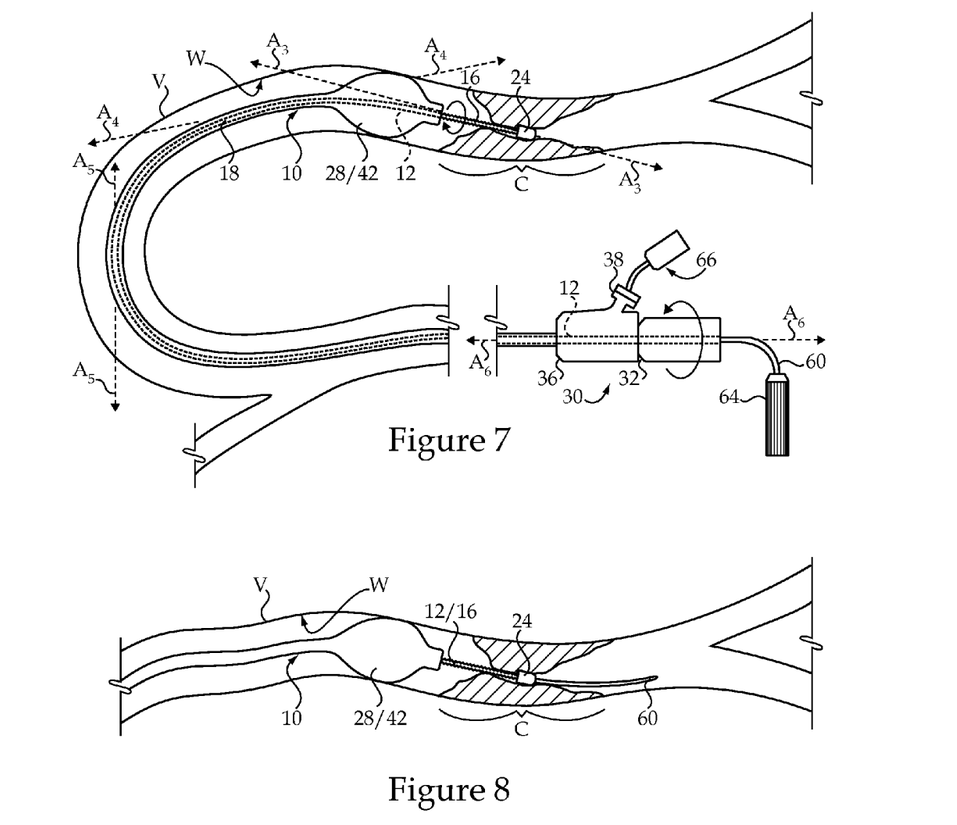
FIG. 7 is a side diagrammatic view of a vascular structure of a patient, at yet another stage of a procedure, according to one embodiment.
FIG. 8 is a side diagrammatic view of a vascular structure of a patient, at yet another stage of a procedure, according to one embodiment.

With mechanism 10 positioned approximately as shown in FIG. 6, and anchor 42 deployed, mechanism 10 may be actuated to advance constriction crossing tip 24 through vascular constriction C. Anchor 42 may be maintained in its deployed state contacting vascular wall W during advancing constriction crossing tip 24. Referring now to FIG. 7, there is shown vascular structure V with mechanism 10 positioned therein as it might appear during rotating first sheath 12 relative to second sheath 18 to advance constriction crossing tip 24 through vascular constriction C. Also shown in FIG. 7 is a fluid supply 66 coupled with fitting 38 and configured to supply inflation fluid to anchoring mechanism 28 in the manner described herein. It will be recalled that rotation of handle 32 relative to handle 36 may cause first sheath 12 to rotate about an axis of rotation relative to second sheath 18. Simultaneously, constriction crossing tip 24 may be advanced in the proximal to distal direction by helically engaging first sheath 12 with second sheath 18. In the embodiments shown, external thread 52 of first sheath 12 may engage with second sheath 18, and in particular may engage with internal thread 54 of second sheath 18. It should be appreciated that mechanism 110 might be used in a manner similar to that presently described with regard to mechanism 10. Where mechanism 110 used, however, advancing constriction crossing tip 124 of first sheath 112 may take place by engaging internal thread 152 of first sheath 112 with external thread 154 of second sheath 118 while rotating second sheath 118.

As mentioned above, first sheath 12 may be rotated about an axis of rotation relative to second sheath 18. In the particular embodiments shown, wire guide 60 has been introduced into vascular structure V by way of a curving path within the patient. Mechanism 10 has been slid over wire guide 60 along a similar curving path. Accordingly, rotating first sheath 12 relative to second sheath 18 may include rotating first sheath 12 simultaneously about a plurality of different axes of rotation in a first direction of relative rotation to advance constriction crossing tip 24 through vascular construction C. A plurality of different axes of rotation $A_3$, $A_4$, $A_5$, $A_6$, are defined by the curving path. Where mechanism 10 extends along a different path than that shown, greater or fewer axes of rotation may exist. Turning now to FIG. 8, there is shown vascular structure V having mechanism 10 positioned therein, where constriction crossing tip 24 has been advanced sufficiently through vascular constriction C such that wire guide 60 may subsequently be passed completely through vascular constriction C by pushing wire guide 60 from a location outside of the patient through mechanism 10. Advancing of wire guide 60 could occur simultaneously with advancing tip 24, or subsequent thereto. In the FIG. 8 illustration, it may be noted that constriction crossing tip 24 has not been advanced completely past vascular constriction C. In some instances, it may be desirable to advance constriction crossing tip 24 relatively further than that shown in FIG. 8, or not as far as that shown in FIG. 8. The actual extent to which constriction crossing tip 24 needs to be advanced into or beyond a vascular constriction may depend upon the geometry, location, and potentially composition, of the particular vascular constriction. It also may be desirable to advance mechanism 10 in a step wise manner. For instance, mechanism 10 could be actuated to move tip 24 a first distance through a constriction, anchoring mechanism 28 could then be deactivated, and re-deployed distally, then mechanism 10 actuated again to move tip 24 a second distance through a constriction.

Figure 9:
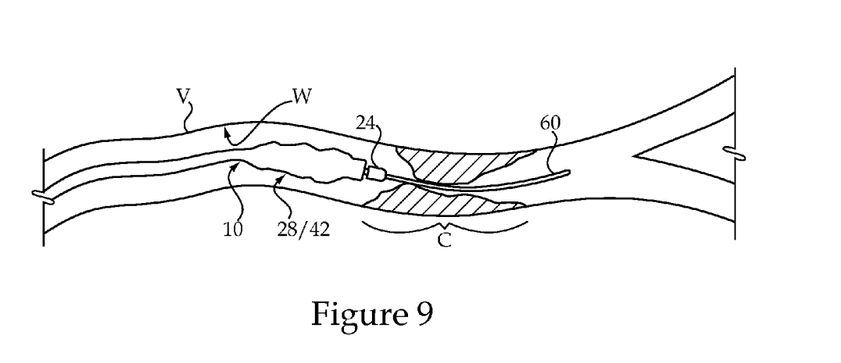
FIG. 9 is a side diagrammatic view of a vascular structure of a patient, at yet another stage of a procedure, according to one embodiment.

In any event, once wire guide 60 has been advanced to a location distal of the vascular constriction, removal of mechanism 10 may commence. Removing mechanism 10 from the patient may include retracting constriction crossing tip 24 by rotating first sheath 12 relative to second sheath 18 simultaneously about the plurality of different axes of rotation shown in FIG. 7 in a reverse direction of relative rotation, and drawing constriction crossing tip 24 in a distal to proximal direction back through and out of vascular constriction C. Referring to FIG. 9, once vascular constriction crossing tip 24 has been retracted out of vascular constriction C, anchoring mechanism 28 may be deactivated, for example by withdrawing inflation fluid therefrom. Removal of mechanism 10 may be completed by sliding mechanism 10 in a distal to proximal direction over wire guide 60 until mechanism 10 is removed from the patient.

Figure 10:
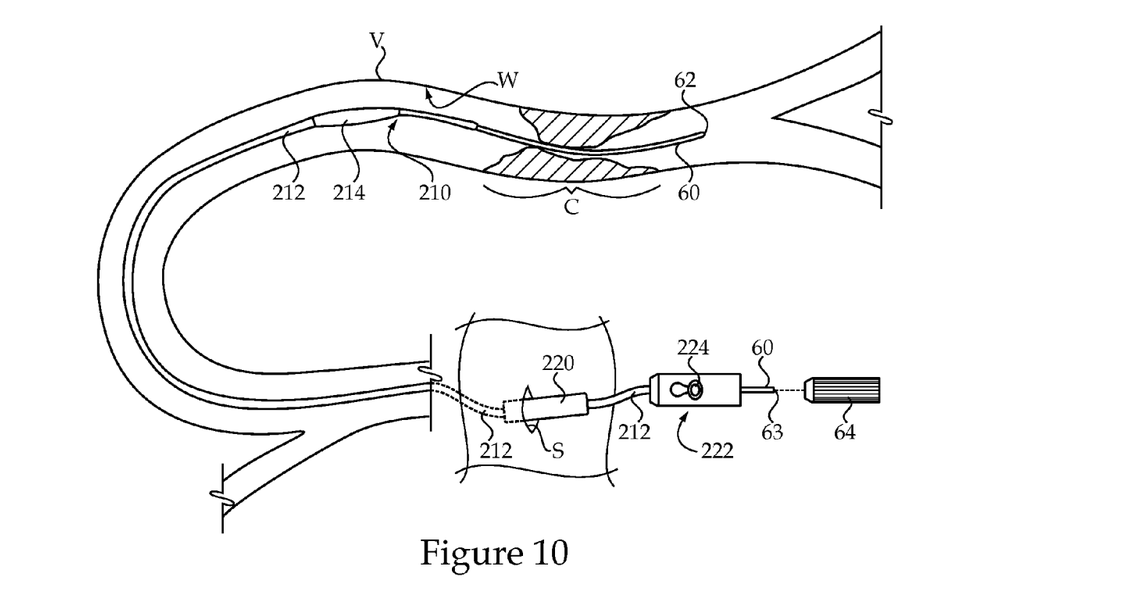
FIG. 10 is a side diagrammatic view of a vascular structure of a patient, at yet another stage of a procedure, according to one embodiment.
Figure 11:
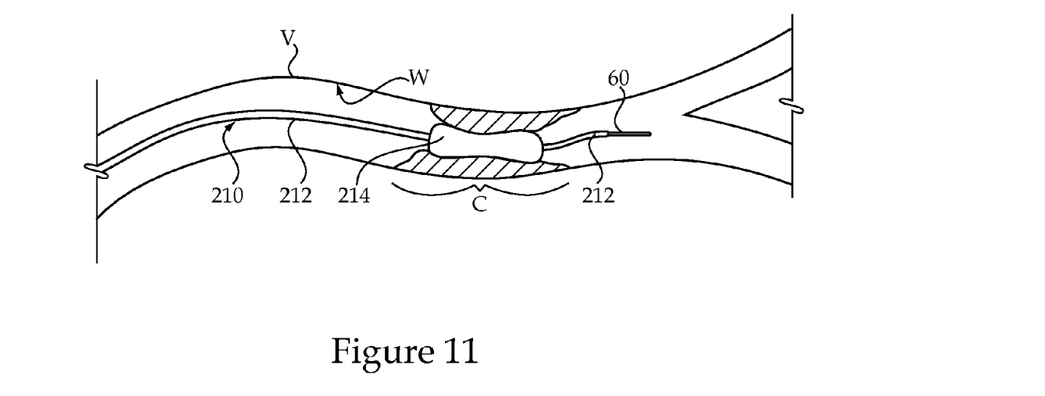
FIG. 11 is a side diagrammatic view of a vascular structure of a patient, at yet another stage of a procedure, according to one embodiment.

With wire guide 60 positioned with wire guide tip 62 at a location distal to vascular constriction C, an intraluminal treatment device may be guided via wire guide 60 to the location distal of vascular constriction C. Referring now to FIG. 10, there is shown an intraluminal treatment device 210 which has been guided in a curving path within the patient toward wire guide tip 62, which is located distal to vascular constriction C. Guiding intraluminal treatment device 210 may take place by sliding intraluminal treatment device 210 over wire guide 60 in the proximal to distal direction subsequent to removing vascular constriction crossing mechanism 10 from the patient. In the embodiments shown, intraluminal treatment device 210 includes a catheter 212, an angioplasty balloon 214 and a handle mechanism 222 having an inflation fluid port 224 located thereon. A dilation sheath 220 is shown traversing an incision S in the patient, and may be employed in a conventional manner. From the configuration shown in FIG. 10, intraluminal treatment device 210 may be further advanced to a location where angioplasty balloon 214 is positioned within vascular constriction C as shown in FIG. 11, such that it can be inflated via conventional techniques to perform an angioplasty procedure on vascular constriction C. The foregoing description focuses on crossing vascular constriction C, then performing a procedure such as angioplasty, also on vascular constriction C. In other instances, the vascular constriction or other target structure or location for performing a procedure might not be constriction C, but could instead include a structure or location distal to constriction C. Thus, vascular constriction C might be merely an obstacle, or one of several obstacles, to be overcome before the actual site of interest may be reached.

While intraluminal treatment device 210 is shown as a conventional angioplasty mechanism, it should be appreciated that a variety of other intraluminal treatment devices may be used as described herein. Moreover, while intraluminal treatment device 210 is shown as a mechanism separate from vascular constriction crossing mechanism 10, it should be appreciated that embodiments are contemplated wherein the features of vascular constriction crossing mechanism 10 and intraluminal treatment device 210 are combined. For example, an additional inflation lumen, and an angioplasty balloon might be coupled with second sheath 18 to enable vascular constriction crossing mechanism 10 to be integrated with an angioplasty device. In still other embodiments, parts of vascular constriction crossing mechanism 10 could fairly be considered themselves to be an intraluminal treatment device. For example, a contrast agent might be supplied to the vicinity of vascular constriction C via delivery through wireguide lumen 34. Thus, the term intraluminal treatment device as used herein should be broadly construed. It should further be appreciated that, while in the embodiments shown wire guide 60 remains within the patient, wire guide 60 might be removed during crossing vascular constriction C with mechanism 10, then re-inserted after tip 24 has crossed vascular constriction C for guiding intraluminal treatment device 210. In some instances, mechanism 10 might itself be used to guide an intraluminal treatment device. For example, with tip 24 positioned distally of constriction C, an intraluminal treatment device would be passed through first sheath 12 to a location distal to constriction C.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For instance, while mechanism 10 is illustrated and described as having a separate lumen 40 for supplying inflation fluid, alternatives are contemplated. Inflation fluid could be supplied through an interior of sheath 18 then into volume 46 via an orifice or the like. In such a design, the inflation fluid and sheath 12 would be passed through the same passage, and threads 52 and 54 could provide a fluid seal. A similar strategy could be used with device 110. Other aspects, features and advantages will be apparent upon an examination of the attached drawings and appended claims.

What is claimed is:

1. A method of performing a percutaneous vascular procedure on a patient comprising the steps of:
    sliding a vascular constriction crossing mechanism in a proximal to distal direction over a wire guide having a wire guide tip positioned at a first location on a proximal side of a vascular constriction;
    rotating one of a first sheath of the vascular constriction crossing mechanism and a second sheath of the vascular constriction crossing mechanism about an axis of rotation relative to the other of the first sheath and the second sheath;
    advancing a constriction crossing tip of the first sheath through the vascular constriction to a second location which is distal to the first location responsive to the rotating step and a helical engagement between threads of the first sheath and threads of the second sheath; and
    guiding an intraluminal treatment device to the second location.

2. The method of claim 1 further comprising a step of removing the vascular constriction crossing mechanism from the patient, wherein the guiding step further includes guiding the intraluminal treatment device in a curving path within the patient at least in part by sliding the intraluminal treatment device over the wire guide in the proximal to distal direction, subsequent to the removing step.

3. The method of claim 2 wherein:
    the step of rotating further includes rotating the one of the first sheath and the second sheath simultaneously about a plurality of different axes of rotation in a first direction of relative rotation; and
    the step of removing the vascular constriction crossing mechanism from the patient further includes retracting the constriction crossing tip from the second location at least in part by rotating one of the first sheath and the second sheath simultaneously about the plurality of different axes of rotation in a reverse direction of relative rotation.

4. The method of claim 3 wherein:
    the rotating step further includes applying a torque to the one of the first sheath and the second sheath;
    the advancing step further includes converting a portion of the torque to an axial force on the first sheath; and
    the method further comprising a step of resisting rotational displacement of the second sheath in response to the torque and resisting axial displacement of the second sheath in response to the axial force, at least in part by contacting a vascular wall of the patient with an anchoring mechanism of the vascular constriction crossing mechanism, during the step of rotating.

5. The method of claim 1 wherein the first sheath has internal threads; and
    the second sheath has external threads that helically engage the internal threads.

6. The method of claim 1 wherein the first sheath has external threads; and
    the second sheath has internal threads that helically engage the external threads.

7. The method of claim 1 including deploying an anchoring mechanism to frictionally engage a vascular wall to resist rotation of the second sheath relative to the vascular wall during the rotating step.

8. The method of claim 7 wherein the step of deploying the anchoring mechanism includes inflating a balloon.

9. The method of claim 1 including advancing the wire guide through the vascular constriction after the constriction crossing tip has been advanced through the vascular constriction.

10. The method of claim 9 including sliding the first sheath and the second sheath in a distal to proximal direction to remove the vascular constriction crossing mechanism from the patient while a distal end of the wire guide remains distally beyond the vascular constriction.

* * * * *